United States Patent
Yamazoe et al.

(10) Patent No.: US 11,584,705 B2
(45) Date of Patent: Feb. 21, 2023

(54) PRODUCTION METHOD FOR CYCLOHEXANEDICARBOXYLIC ACID COMPOUND, DICYANOCYCLOHEXANE COMPOUND AND BIS(AMINOMETHYL)CYCLOHEXANE COMPOUND

(71) Applicant: Mitsubishi Gas Chemical Company, Inc., Chiyoda-ku (JP)

(72) Inventors: Aoi Yamazoe, Niigata (JP); Yuta Ohmori, Kamisu (JP); Akifumi Iida, Niigata (JP); Yutaka Kanbara, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 199 days.

(21) Appl. No.: 17/043,347

(22) PCT Filed: Apr. 11, 2019

(86) PCT No.: PCT/JP2019/015724
§ 371 (c)(1),
(2) Date: Sep. 29, 2020

(87) PCT Pub. No.: WO2019/198778
PCT Pub. Date: Oct. 17, 2019

(65) Prior Publication Data
US 2021/0024445 A1    Jan. 28, 2021

(30) Foreign Application Priority Data

Apr. 11, 2018 (JP) .............................. JP2018-076283

(51) Int. Cl.
C07C 51/36 (2006.01)
C07C 209/48 (2006.01)
C07C 253/22 (2006.01)
C07C 51/41 (2006.01)

(52) U.S. Cl.
CPC .............. C07C 51/36 (2013.01); C07C 51/41 (2013.01); C07C 209/48 (2013.01); C07C 253/22 (2013.01)

(58) Field of Classification Search
None
See application file for complete search history.

(56) References Cited

U.S. PATENT DOCUMENTS

| | | | |
|---|---|---|---|
| 5,118,841 A | 6/1992 | Cook et al. | |
| 5,202,475 A | 4/1993 | Cook et al. | |
| 6,541,662 B2* | 4/2003 | Machida | C07C 51/36 562/509 |
| 10,906,865 B2* | 2/2021 | Iida | C07C 51/36 |
| 11,352,318 B2* | 6/2022 | Iida | C07C 209/48 |
| 2013/0197269 A1 | 8/2013 | Yoshimura et al. | |
| 2013/0197270 A1 | 8/2013 | Yoshimura et al. | |
| 2019/0225572 A1 | 7/2019 | Iida et al. | |
| 2020/0165195 A1* | 5/2020 | Iida | C07C 253/22 |

FOREIGN PATENT DOCUMENTS

| | | |
|---|---|---|
| CN | 101591237 A | 12/2009 |
| CN | 103153940 A | 6/2013 |
| CN | 105016944 A | 11/2015 |
| CN | 105377808 A | 3/2016 |
| EP | 2 626 343 A1 | 8/2013 |
| EP | 2 626 344 A1 | 8/2013 |
| EP | 3 029 022 A1 | 6/2016 |
| EP | 3 733 643 A1 | 11/2020 |
| EP | 3 778 544 A1 | 2/2021 |
| JP | 7-507041 A | 8/1995 |
| JP | 2002-20346 A | 1/2002 |
| JP | 2011-6382 A | 1/2011 |
| JP | 5562429 B2 | 7/2014 |
| JP | 5640093 B2 | 12/2014 |
| WO | WO 2018/066447 A1 | 4/2018 |
| WO | WO 2019/035381 A1 | 2/2019 |

OTHER PUBLICATIONS

Machine generated translation of CN101591237, published on Dec. 2, 2009. (Year: 2009).*
Thomas H. Strickland et al., " Preparation of Ammonium 1,4-cyclohexanedicarboxylate", UST883022, Feb. 23, 1971, XP055795436, pp. 1-1.
International Search Report dated June 25, 2019 in PCT/JP2019/015724 filed on April 11, 2019, 2 pages.
Tian, "Unit Process of Organic Synthesis", Chemical Industry Press Co., Ltd., Jul. 1999, p. 146 (3 total pages).

* cited by examiner

*Primary Examiner* — Amy C Bonaparte
(74) *Attorney, Agent, or Firm* — Oblon, McClelland, Maier & Neustadt, L.L.P.

(57) ABSTRACT

A production method for a cyclohexanedicarboxylic acid compound, having a step of obtaining a cyclohexanedicarboxylic acid compound or an aqueous ammonia solution of a cyclohexanedicarboxylic acid compound by bringing a phthalic acid compound in an aqueous ammonia solution into contact with hydrogen in the presence of a fixed bed catalyst in a reactor.

20 Claims, No Drawings

PRODUCTION METHOD FOR CYCLOHEXANEDICARBOXYLIC ACID COMPOUND, DICYANOCYCLOHEXANE COMPOUND AND BIS(AMINOMETHYL)CYCLOHEXANE COMPOUND

TECHNICAL FIELD

The present invention relates to production methods for a cyclohexanedicarboxylic acid compound, a dicyanocyclohexane compound and a bis(aminomethyl)cyclohexane compound.

BACKGROUND ART

A bis(aminomethyl)cyclohexane compound is an industrially important compound, which is used as a raw material for an epoxy curing agent, polyamide, polyurethane, etc.

There are several production methods for a bis(aminomethyl)cyclohexane compound. As a specific production method, a method has been known in which a hydrogenation reaction is performed on a phthalic acid compound to create a cyclohexanedicarboxylic acid compound, amidation and dehydration are performed on the cyclohexanedicarboxylic acid compound to create a dicyanocyclohexane compound, and a hydrogenation reaction is performed on the dicyanocyclohexane compound to create a bis(aminomethyl)cyclohexane compound. Here, in order to produce a cyclohexanedicarboxylic acid compound, methods as described in Patent Literatures 1 to 3 have been used.

CITATION LIST

Patent Literature

Patent Literature 1: Japanese Patent Application Laid-Open No. 2011-006382
Patent Literature 2: Japanese Translation of PCT International Application Publication No. 1995-507041
Patent Literature 3: Japanese Patent Application Laid-Open No. 2002-020346

SUMMARY OF INVENTION

Technical Problem

Patent Literature 1 describes that the reaction mode is preferably a liquid phase suspension reaction mode because the solubility of terephthalic acid or a derivative thereof in a general purpose solvent such as water is not high. However, in such a method, the catalyst is mixedly present in a large amount in the reaction solution after the reaction, and therefore, it takes time to filter out the catalyst. In addition, due to the low solubility of the product in the reaction solution, it is necessary to carry out thermal filtration or filtration after induction into an alkali salt, and the production efficiency is thus not sufficient.

On the other hand, Patent Literatures 2 and 3 describe that phthalic acid or a derivative thereof is changed into an alkali salt in order to improve the solubility thereof. However, in this case, a neutralization step is required after the reaction, and the production efficiency is thus not sufficient even by this method.

The present invention has been made in light of the circumstances described above, and has an object to provide a novel production method for a cyclohexanedicarboxylic acid compound that is excellent in the production efficiency. Furthermore, the present invention has an object to provide production methods for a dicyanocyclohexane compound and a bis(aminomethyl)cyclohexane compound that are obtained via the production method.

Solution to Problem

The present inventors have made diligent researches in order to achieve the objects described above, and consequently have found that the objects described above can be achieved by bringing a phthalic acid compound in an aqueous ammonia solution into contact with hydrogen and a fixed bed catalyst in a reactor, leading to completion of the present invention.

More specifically, the present invention is as follows:
(1)
A production method for a cyclohexanedicarboxylic acid compound, having a step of obtaining a cyclohexanedicarboxylic acid compound or an aqueous ammonia solution of a cyclohexanedicarboxylic acid compound by bringing a phthalic acid compound in an aqueous ammonia solution into contact with hydrogen in the presence of a fixed bed catalyst in a reactor.
(2)
A production method for a dicyanocyclohexane compound, having a step of obtaining a dicyanocyclohexane compound by subjecting the cyclohexanedicarboxylic acid compound or a heated concentrate of the aqueous ammonia solution of a cyclohexanedicarboxylic acid compound obtained via the production method for a cyclohexanedicarboxylic acid compound according to (1) to a cyanation reaction.
(3)
The production method for a dicyanocyclohexane compound according to (2), wherein at least a part of the aqueous ammonia solution of a cyclohexanedicarboxylic acid compound obtained in the step of obtaining a cyclohexanedicarboxylic acid compound is used as an ammonia source for the step of obtaining a dicyanocyclohexane compound.
(4)
The production method for a dicyanocyclohexane compound according to (2) or (3), further having a step of obtaining the heated concentrate by heating the aqueous ammonia solution of a cyclohexanedicarboxylic acid compound to 100 to 200° C. to remove at least a part of water.
(5)
A production method for a bis(aminomethyl)cyclohexane compound, having a step of obtaining a bis(aminomethyl)cyclohexane compound by subjecting the dicyanocyclohexane compound obtained via the production method according to any of (2) to (4) to a hydrogenation reaction.

Advantageous Effects of Invention

According to the present invention, a novel production method for a cyclohexanedicarboxylic acid compound that is excellent in the production efficiency can be provided. Furthermore, according to the present invention, production methods for a dicyanocyclohexane compound and a bis(aminomethyl)cyclohexane compound that are obtained via the production method can be provided.

DESCRIPTION OF EMBODIMENTS

Hereinafter, an embodiment for performing the present invention (hereinafter, simply referred to as a "present embodiment") will be described in detail, but the present invention is not limited to the present embodiment described below. It is possible to make various modifications to the present invention within a range of not departing from its spirit.

[Production Method for a Cyclohexanedicarboxylic Acid Compound]

A production method for a cyclohexanedicarboxylic acid compound of the present embodiment (hereinafter, also referred to as a "CHDA production method") has a step (hereinafter, also referred to as a "nucleus hydrogenation step") of obtaining a cyclohexanedicarboxylic acid compound or an aqueous ammonia solution of a cyclohexanedicarboxylic acid compound by bringing a phthalic acid compound in an aqueous ammonia solution into contact with hydrogen in the presence of a fixed bed catalyst in a reactor. In the production method of the present embodiment, by changing the phthalic acid compound into an ammonium salt in the aqueous ammonia solution, the solubility in water is improved, and as a result, a reaction in a fixed bed mode is enabled. Therefore, a step for filtering the catalyst becomes unnecessary, and the production efficiency thus becomes excellent. In addition, by taking out the phthalic acid compound as the ammonium salt as is, and by using it for a cyanation step, which is the subsequent step, a neutralization step is not required and effective utilization of ammonia is also enabled, and the production efficiency thus becomes further excellent.

In the present embodiment, the "cyclohexanedicarboxylic acid compound" refers to a concept including cyclohexanedicarboxylic acid and a derivative thereof, and a cyclohexanedicarboxylic acid derivative also includes a salt form thereof. Examples of the cyclohexanedicarboxylic acid compounds include 1,2-cyclohexanedicarboxylic acid, 1,3-cyclohexanedicarboxylic acid and 1,4-cyclohexanedicarboxylic acid. Examples of the derivative of cyclohexanedicarboxylic acid include an ammonium salt of cyclohexanedicarboxylic acid such as an ammonium salt of 1,2-cyclohexanedicarboxylic acid, an ammonium salt of 1,3-cyclohexanedicarboxylic acid, an ammonium salt of 1,4-cyclohexanedicarboxylic acid; and carboxamidocyclohexanecarboxylic acid such as 2-carboxamidocyclohexane-1-carboxylic acid, 3-carboxamidocyclohexane-1-carboxylic acid and 4-carboxamidocyclohexane-1-carboxylic acid.

On the other hand, examples of the derivative of cyclohexanedicarboxylic acid include a derivative having two carboxamide groups in the molecule, such as 1,2-cyclohexanedicarboxamide, 1,3-cyclohexanedicarboxamide and 1,4-cyclohexanedicarboxamide. However, the derivative having two carboxamide groups described above has a high melting point and is difficult to be dissolved upon the cyanation reaction, leading to a decrease in reactivity. As a result, a byproduct having high boiling point is likely to be formed and the yield tends to be deteriorated. Therefore, the content of the derivative having two carboxamide groups described above in the cyclohexanedicarboxylic acid compound is preferably 10% by mass or less, more preferably 5% by mass or less, and still more preferably 1% by mass or less. On the other hand, the total content of cyclohexanedicarboxylic acids, ammonium salts of cyclohexanedicarboxylic acids and carboxamidocyclohexanecarboxylic acids in the cyclohexanedicarboxylic acid compound is preferably 90% by mass or more, more preferably 95% by mass or more, and still more preferably 99% by mass or more from the viewpoint of yield and reactivity.

In the present embodiment, the "phthalic acid compound" refers to phthalic acid, phthalic anhydride, isophthalic acid and terephthalic acid, as well as a derivative thereof, and further refers to a concept also including a salt form (for example, an ammonium salt).

In the nucleus hydrogenation step, for example, a reactor is first filled with a catalyst. The reactor is not particularly limited as long as the tower functions as a fixed bed in such a way that the liquid reaction solution passes over the catalyst to provide a gas-liquid-solid mass transfer state. In addition, the catalyst referred to here may be, for example, a catalyst used for an ordinary nucleus hydrogenation reaction that has been reduced by a publicly known method, or that has not been reduced yet. For the catalyst, for example, a catalyst used for an ordinary nucleus hydrogenation reaction can be employed, and more particularly, one or two or more metal catalysts or precious metal catalysts, such as Ru, Pd, Pt and Rh, are used. In addition, the catalyst may have a form in which the metal catalyst described above is supported on one or two or more supports that are ordinarily used, such as carbon, $Al_2O_3$, $SiO_2$, $SiO_2$—$Al_2O_3$, $TiO_2$ and $ZrO_2$. When a support is used, it is preferable that the amount of the catalyst to be supported be 0.1 to 10% by mass based on 100% by mass of the support.

In the nucleus hydrogenation step, next, hydrogen gas is introduced until the pressure reaches a predetermined pressure and the temperature is elevated to a predetermined temperature. The hydrogen gas is then introduced into the reactor at a predetermined flow rate. The pressure in the reaction tube may be an ordinary pressure or may be compressed. When compressed, the pressure in the system is preferably 0.5 to 15 MPa and the reaction temperature is preferably 40 to 150° C. The flow rate of hydrogen is preferably an amount such that hydrogen is 300 to 1000 mol %, and more preferably 300 to 600 mol % based on 100 mol % of the phthalic acid compound that comes into contact with the catalyst per unit time.

In the nucleus hydrogenation step, next, an aqueous ammonia solution of the phthalic acid compound (hereinafter, also referred to as a "reaction solution") is formulated and the reaction solution is distributed in the reactor using a pump. The amount of the phthalic acid compound to be placed is preferably 2 to 20% by mass based on the entire reaction solution. In addition, the amount of ammonia in the aqueous ammonia solution to be placed is preferably 200 to 400 mol % based on 100 mol % of the phthalic acid compound. Here, when the phthalic acid compound is an ammonium salt, the amount of ammonia to be placed (mol %) also includes the amount of ammonia contained in the phthalic acid compound. There is no limitation on the amount of the catalyst to be used, and it may be appropriately determined to achieve the target conversion rate, considering the content of the supported metal catalyst and the amount of the phthalic acid compound used for the reaction. In addition, the reaction time may be any length as long as it is long enough for the nucleus hydrogenation reaction to progress sufficiently. By adjusting each reaction condition to be within the range described above, there is a tendency that the yield and selectivity of the cyclohexanedicarboxylic acid compound to be obtained can be enhanced.

When the cyclohexanedicarboxylic acid compound is produced in a manner as mentioned above, the reaction solution includes an aqueous ammonia solution and the produced cyclohexanedicarboxylic acid compound.

A production method for a dicyanocyclohexane compound of the present embodiment (hereinafter, also referred to as a "CHDN production method") has a step (hereinafter, also referred to as a "cyanation step") of obtaining a dicyanocyclohexane compound by subjecting the cyclohexanedicarboxylic acid compound or a heated concentrate of the aqueous ammonia solution of a cyclohexanedicarboxylic acid compound (hereinafter, also simply referred to as a "heated concentrate") obtained via the above-mentioned production method for a cyclohexanedicarboxylic acid compound of the present embodiment to a cyanation reaction. Here, the heated concentrate refers to a concept including the aqueous ammonia solution of a cyclohexanedicarboxylic acid compound or crystals obtained through filtration, and a mixture (slurry) thereof.

By using the heated concentrate for the cyanation step, the yield of the dicyanocyclohexane compound can be increased compared to the case where, for example, cyanation is performed only by introducing ammonia gas into the system. The main cause is believed to be, without being limited to, that the heating in a heat concentration step, which will be mentioned later, produces an intermediate in the heated concentrate and this intermediate contributes to the cyanation reaction.

In the present embodiment, the "dicyanocyclohexane compound" refers to a concept including dicyanocyclohexane and a derivative thereof. Examples of the dicyanocyclohexane compounds include 1,2-dicyanocyclohexane, 1,3-dicyanocyclohexane and 1,4-dicyanocyclohexane.

In the CHDN production method of the present embodiment, it is preferable to use at least a part of the aqueous ammonia solution of cyclohexanedicarboxylic acid obtained in the step of obtaining a cyclohexanedicarboxylic acid compound as an ammonia source for the step of obtaining a dicyanocyclohexane compound. By doing this, the effective utilization of ammonia is enabled. In particular, from the viewpoint of effective utilization of ammonia, it is desirable to use 5 to 25% by mass of the obtained aqueous ammonia solution of cyclohexanedicarboxylic acid as the ammonia source.

It is preferable that the CHDN production method of the present embodiment further have a step (hereinafter, also referred to as a "heat concentration step") of obtaining the heated concentrate by heating the aqueous ammonia solution of a cyclohexanedicarboxylic acid compound to remove at least a part of water. By doing this, the yield of the dicyanocyclohexane compound in the cyanation step tends to be further increased. It is preferable that the temperature upon the heat concentration (heating temperature) be 30 to 200° C. When the heating temperature is within the range described above, water can be effectively removed via volatilization from the aqueous ammonia solution, and as a result, the yield of dicyanocyclohexane in the cyanation step, which will be mentioned later, tends to be further increased. From the same viewpoint, the heating temperature is more preferably 50 to 200° C. and still more preferably 100 to 200° C. On the other hand, when the cyclohexanedicarboxylic acid derivative is 1,4-cyclohexanedicarboxylic acid derivative, from the viewpoint of increasing the content of trans isomer of the 1,4-cyclohexanedicarboxylic acid derivative, the heating temperature is preferably 120 to 200° C. and more preferably 140 to 200° C. The pressure may be an ordinary pressure or may be compressed. It is preferable that the pressure upon the heat concentration be 0.003 to 2 MPa from the viewpoint of effectively removing water via volatilization from the aqueous ammonia solution.

In addition, in the present embodiment, the use of the heated concentrate described above for the cyanation step is useful in that ammonia present in the heated concentrate can be used effectively as a raw material for the cyanation reaction.

In the CHDN production method of the present embodiment, the heat concentration step may be carried out prior to the cyanation step. In the heat concentration step, it is preferable that the concentration of the cyclohexanedicarboxylic acid compound in the aqueous ammonia solution after the heat concentration be 25 to 100 mol % based on 100 mol % of ammonia.

In the heat concentration step, the method of heat concentration is not particularly limited as long as water can be removed via volatilization from the aqueous ammonia solution of a cyclohexanedicarboxylic acid compound. For the method of heat concentration, from the viewpoint of positively removing water via volatilization from the aqueous ammonia solution of a cyclohexanedicarboxylic acid compound to the outside of the system, a method utilizing an open system is preferable.

The heat concentration step may be performed sequentially with the subsequent cyanation step. That is, the aqueous ammonia solution of a cyclohexanedicarboxylic acid compound, water as necessary, and a catalyst are placed in a reactor at first; and an inert gas is introduced until the pressure in the system reaches a predetermined pressure, optionally along with ammonia gas as necessary. Then, in order to maintain the pressure in the reactor within a constant range while retaining the temperature in the reactor preferably within a range of 100° C. to 200° C., the inert gas is introduced into the reactor or the gas in the reactor is discharged, appropriately, thereby obtaining a heated concentrate.

After this, the cyanation reaction may be advanced by introducing ammonia gas into the reactor as necessary and adjusting the temperature and pressure in the reactor to be a temperature and pressure required for the cyanation step. In this case, it is preferable to set an occasion to introduce ammonia gas after obtaining the heated concentrate because by doing this, ammonia can be utilized more efficiently. Examples of the inert gas described above include, for example, nitrogen gas, as well as noble gases, such as argon and helium. However, the inert gas does not have to be introduced into the system.

In addition, in the heat concentration step, crystals may be taken out from the heated concentrate and used as a raw material for the subsequent cyanation step. Examples of the collection method include a method in which the heated concentrate is filtered to collect crystals. From the viewpoint of operability, the liquid content of mother liquor in the 1,4-cyclohexanedicarboxylic acid derivative after the filtration is preferably 5 to 35% by mass, and more preferably 10 to 25% by mass. The 1,4-cyclohexanedicarboxylic acid derivative after the filtration may be subjected to the subsequent step in a state containing the mother liquor, or it may be subjected to the subsequent step after the crystals are once taken out and dried. In addition, the number of times of the heat concentration step may be once, or it may be multiple times. In the production method of the present embodiment, the aqueous ammonia solution from which the crystals have been collected by the first heat concentration step can be repeatedly used in the second and subsequent heat concentration steps in order to further collect the crystals. In the production method of the present embodiment, since the number of times of the heat concentration step is multiple times, thereby fully collecting the cyclohexanedicarboxylic acid compound, the yield of the cyclohexanedicarboxylic acid compound tends to be further excellent.

In the cyanation step, the heated concentrate, water as necessary, and a catalyst are placed in a reactor at first; and an inert gas is introduced until the pressure in the system reaches a predetermined pressure. Then, the inside of the reactor is heated to a predetermined temperature, and the inert gas is appropriately introduced into the reactor in order to maintain the pressure in the reactor within a constant range while stirring the inside of the reactor, thereby advancing the cyanation reaction.

For the catalyst, either homogeneous catalyst or heterogeneous catalyst can be used. As the catalyst, a catalyst used for an ordinary cyanation reaction can be employed, and more particularly, examples of the catalyst include a metal oxide, such as silica gel, alumina, silica alumina, zinc oxide, tin oxide, iron oxide, titanium oxide, zirconium oxide, hafnium oxide, manganese oxide, tungsten oxide, vanadium pentoxide, niobium pentoxide, tantalum oxide, gallium oxide, indium oxide and scandium oxide. These may be a simple substance, a complex oxide, or those supported on a support. Examples of the supported component include, for example, an alkali metal such as sodium, lithium, potassium, rubidium and cesium, tin, rhenium, manganese, molybdenum, tungsten, vanadium, iron, nickel, chromium, boric acid, hydrochloric acid and phosphoric acid. In addition, examples of the catalyst also include a rhenium compound such as perrhenic acid and rhenium oxide, an organic tin compound such as dibutyltin oxide, a ruthenium compound such as dichlorotris(triphenylphosphine)ruthenium (II), and cobalt oxide. Among these, zinc oxide and tin oxide are preferable from the viewpoint of advancing the cyanation reaction more effectively and reliably. These catalysts are used alone as one kind or in combination of two or more kinds. Furthermore, it is preferable that the amount of the catalyst to be used be 0.5 to 20% by mass based on 100% by mass of the cyclohexanedicarboxylic acid compound. By using the catalyst in an amount within the range described above, there is a tendency that the yield and selectivity of the dicyanocyclohexane compound to be obtained can be enhanced.

In the cyanation step, no solvent may be used or a solvent may be used. It is preferable to use a solvent with a boiling point of 600° C. or less, more preferable to use a solvent with a boiling point of 500° C. or less, and still more preferable to use a solvent with a boiling point of 420° C. or less. Also, the solvent has a boiling point, which is equal to or higher than the reaction temperature of the cyanation reaction, of preferably 250° C. or more, more preferably 270° C. or more, and still more preferably 300° C. or more. When the boiling point is 300° C. or higher, the cyanation reaction progresses smoothly, and production of impurities such as a trimer of dicyanocyclohexane can often be suppressed. Specific examples of the solvent to be used in the cyanation step include: an aliphatic alkane such as heptadecane, nonadecane and docosane; an aliphatic alkene such as heptadecene, nonadecene and docosene; aliphatic alkyne such as heptadecyne, nonadecyne and docosyne; an alkyl-substituted aromatic such as alkylbenzene including undecylbenzene, tridecylbenzene and tetradecylbenzene, dialkylbenzene and alkylnaphthalene; an acid or acid anhydride such as 2,5-dichlorobenzoic acid and tetrachlorophthalic anhydride; an amide compound such as undecaneamide, lauric acid amide and stearic acid amide; a nitrile compound such as tetradecanenitrile, hexadecanenitrile, 2-naphthylacetonitrile, stearonitrile and 1,4-dicyanocyclohexane; a phosphorus compound such as p-chlorodiphenylphosphine and triphenyl phosphite; an amine such as 1,2-diphenylethylamine and trioctylamine; a hydroxide such as 2,2'-biphenol and triphenylmethanol; an ester such as benzyl benzoate and dioctyl phthalate; an ether such as 4-dibromophenyl ether; a halogenated benzene such as 1,2,4,5-tetrachloro-3-nitrobenzene and 4,4'-dichlorobenzophenone; a ketone such as 2-phenylacetophenone and anthraquinone; and triphenylmethane. Among these, an alkylnaphthalene, triphenylmethane or dicyanocyclohexane is preferable from the viewpoint of being not likely to hinder progress of the cyanation reaction.

In addition, ammonia gas may be introduced into the reactor appropriately. Its flow rate may be appropriately adjusted according to the scale of reaction and the like, and normally, it is 0.1 to 5 moles per hour, preferably 0.3 to 4 moles per hour, and more preferably 0.5 to 3 moles per hour based on 1 mole of the cyclohexanedicarboxylic acid compound. It is preferable that the amount of the ammonia gas to be used be 200 to 1000 mol % based on 100 mol % of the cyclohexanedicarboxylic acid compound. By doing this, there is a tendency that the yield and selectivity of the dicyanocyclohexane compound to be obtained can be enhanced.

The reaction temperature in the production method of the present embodiment is not particularly limited as long as it is a temperature at which the cyanation reaction progresses, and it is preferably 270 to 400° C., more preferably 280° C. to 380° C., and still more preferably 290° C. to 350° C. The reaction pressure in the production method of the present embodiment may be a negative pressure, an ordinary pressure or a positive pressure. The reaction time may be any length as long as it is long enough for the cyanation reaction to progress sufficiently. By adjusting the concentration of each raw material and the reaction conditions to be within the ranges mentioned above, there is a tendency that the yield of the dicyanocyclohexane compound can be enhanced.

The dicyanocyclohexane compound may be collected by distilling the reaction solution including the dicyanocyclohexane compound thus obtained, as necessary (hereinafter, this step is referred to as a "distillation step"). The distillation is performed by, for example, heating a distillation apparatus from the bottom section such that the pressure in the system in the distillation apparatus is 3.0 kPa to 4.0 kPa and the temperature is 180 to 230° C., and by cooling the top section, thereby performing gas-liquid contact in the apparatus. By doing this, the dicyanocyclohexane compound can be selectively drawn and collected from the top section of the distillation apparatus.

A production method for a bis(aminomethyl)cyclohexane compound of the present embodiment has a step (hereinafter, also referred to as a "nitrile hydrogenation step") of obtaining a bis(aminomethyl)cyclohexane compound by subjecting the dicyanocyclohexane compound obtained as mentioned above to a hydrogenation reaction (hereinafter, also referred to as a "nitrile hydrogenation reaction").

In the present embodiment, the "bis(aminomethyl)cyclohexane compound" refers to a concept including bis(aminomethyl)cyclohexane and a derivative thereof. Examples of the bis(aminomethyl)cyclohexane compounds include 1,2-bis(aminomethyl)cyclohexane, 1,3-bis(aminomethyl)cyclohexane and 1,4-bis(aminomethyl)cyclohexane.

In the nitrile hydrogenation step, the dicyanocyclohexane compound, a solvent, and a catalyst are placed in a reactor at first; and hydrogen gas is introduced until the pressure in the system reaches a predetermined pressure. Then, the inside of the reactor is heated to a predetermined temperature, and hydrogen gas is appropriately introduced into the reactor in order to maintain the pressure in the reactor within a constant range, thereby advancing the nitrile hydrogenation reaction.

For the solvent, a solvent used for an ordinary nitrile hydrogenation reaction can be employed, and more particularly, examples of the solvent include an alcohol, such as methanol, ethanol, 1-propanol, 2-propanol, 1-butanol, 2-butanol and tert-butanol; an aromatic hydrocarbon, such as meta-xylene, mesitylene and pseudocumene; liquid ammonia; and aqueous ammonia. These solvents are used alone as one kind or in combination of two or more kinds. In addition, for the catalyst, for example, a catalyst used for an ordinary nitrile hydrogenation reaction can be employed, and more particularly, a catalyst containing Ni and/or Co can be used. Generally, for the catalyst, a catalyst made by supporting Ni and/or Co onto $Al_2O_3$, $SiO_2$, diatomaceous earth, $SiO_2$—$Al_2O_3$ or $ZrO_2$ by a precipitation method, Raney nickel, or Raney cobalt is suitably used. Among these, the Raney cobalt catalyst and Raney nickel catalyst are preferable from the viewpoint of advancing the nitrile hydrogenation reaction more effectively and reliably. These catalysts are used alone as one kind or in combination of two or more kinds. Furthermore, the amount of the catalyst to be used is preferably 0.1 to 150% by mass, more preferably 0.1 to 20% by mass, and still more preferably 0.5 to 15% by mass based on 100% by mass of CHDN. By using the catalyst in an amount within the range described above, there is a tendency that the yield and selectivity of the bis(aminomethyl)cyclohexane compound to be obtained can be enhanced.

The concentration of the dicyanocyclohexane compound in the nitrile hydrogenation step is preferably 1 to 50% by mass and more preferably 2 to 40% by mass based on the entire amount of the reaction solution from the viewpoint of reaction efficiency. In addition, the reaction temperature in the nitrile hydrogenation step is preferably 40 to 150° C., and the reaction pressure is preferably 0.5 to 15 MPa in terms of the hydrogen partial pressure. Note that the reaction time may be any length as long as it is long enough for the nitrile hydrogenation reaction to progress sufficiently. By adjusting the reaction conditions to be within the ranges mentioned above, there is a tendency that the yield and selectivity of the bis(aminomethyl)cyclohexane compound to be obtained can be enhanced.

EXAMPLES

Hereinafter, the present invention will be further described in detail with reference to Examples, but the present invention is not limited to these Examples.

Example 1

First Stage of Nucleus Hydrogenation Step

A tubular reactor having an inner diameter of 17 mm was filled with 12.63 g of 2% Ru/C catalyst (average particle diameter (on a volume basis): 0.84 to 2.00 mm) as a fixed bed catalyst. Note that the catalyst described above was used after being reduced at 250° C. for 2 hours in a predetermined reduction apparatus. Hydrogen gas was introduced such that the pressure in the packed tower was 7 MPaG and the hydrogen flow rate was 15 NmL/min during the reaction. The reaction temperature was set at 90° C. and a 28% aqueous ammonia solution of terephthalic acid having a concentration of 8% by mass was continuously fed into the packed tower at a rate of 15.44 g/hour for 60 hours. The supply rate of terephthalic acid to the fixed bed catalyst was 1.235 g (0.0074 mol) per hour. The reaction solution after 60 hours was analyzed by HPLC (product name "Prominence" manufactured by Shimadzu Corporation; column: model name "VG-50 4E" from Shodex; conditions:eluent:0.25 mass % aqueous ammonia solution, flow rate 0.6 mL/min, column temperature 50° C., photodiode array detector). As a result, the conversion rate of terephthalic acid was 100%, the selectivity of 1,4-cyclohexanedicarboxylic acid was 99.9%, the yield was 99.9%, and the proportion of trans isomer of 1,4-cyclohexanedicarboxylic acid (trans ratio) was 24%.

Second Stage of Nucleus Hydrogenation Step

Subsequently, the raw material was fed for 100 hours continuously from the first stage described above except that the temperature was set at 60° C., the pressure was set at 8 MPaG, the hydrogen flow rate was set at 15 NmL/min, and the supply rate of the raw material was set at 15.22 g/hour. The proportion of PTA during the feeding was 1.345 g (0.0081 mol) per hour. Upon analyzing the reaction solution after 160 hours from the start of distribution in the first stage, the conversion rate of terephthalic acid was 100%, the selectivity of 1,4-cyclohexanedicarboxylic acid was 99.8%, the yield was 99.9%, and the proportion of trans isomer of 1,4-cyclohexanedicarboxylic acid (trans ratio) was 20%.

Third Stage of Nucleus Hydrogenation Step

Subsequently, the raw material was fed for 76 hours continuously from the second stage described above except that the temperature was set at 70° C., the pressure was set at 3 MPaG, the hydrogen flow rate was set at 15 NmL/min, and the supply rate of the raw material was set at 15.30 g/hour. The proportion of PTA during the feeding was 1.510 g (0.0091 mol) per hour. Upon analyzing the reaction solution after 236 hours from the start of distribution in the first stage, the conversion rate of terephthalic acid was 100%, the selectivity of 1,4-cyclohexanedicarboxylic acid was 99.9%, the yield was 97.3%, and the proportion of trans isomer of 1,4-cyclohexanedicarboxylic acid (trans ratio) was 22%.

Fourth Stage of Nucleus Hydrogenation Step

Subsequently, the raw material was fed for 1115 hours continuously from the third stage described above except that the temperature was set at 75° C., the pressure was set at 5 MPaG, the hydrogen flow rate was set at 18 NmL/min, and the supply rate of the raw material was set at 26.60 g/hour. The proportion of PTA during the feeding was 1.609 g (0.0097 mol) per hour. Upon analyzing the reaction solution after 1351 hours from the start of distribution in the first stage, the conversion rate of terephthalic acid was 100%, the selectivity of 1,4-cyclohexanedicarboxylic acid was 99.9%, the yield was 99.9%, and the proportion of trans isomer of 1,4-cyclohexanedicarboxylic acid (trans ratio) was 22%.

Heat Concentration Step

In a 300 ml pressure resistant vessel made of SUS316 equipped with a stirring blade, a thermocouple, a pressure gauge, a condenser and a receiver, 155.58 g of the reaction solution produced in Example 1 was placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.91 MPaG, and the internal pressure during the distillation was 0.71 MPaG. At the stage where the amount of distillation reached 105.23 g, the heating was stopped and the reaction solution was cooled to 45° C. After the internal temperature reached 45° C., the reaction solution was filtered and the crystal and the mother liquor were collected. The weight of the obtained crystal after vacuum drying was 3.04 g, and the content of ammonia in the ammonium salt of 1,4-cyclohexanedicarboxylic acid was 0.06 in a molar ratio based on the content of 1,4-cyclohexanedicarboxylic acid in the ammonium salt of 1,4-cyclohexanedicarboxylic acid. The content of trans isomer in the 1,4-cyclohexanedicarboxylic acid derivative was 96%. The weight of the obtained mother liquor was 40.92 g.

Cyanation Step

Example 2

In a 500 mL five neck flask equipped with a stirring blade, a gas introduction tube, a thermocouple and a dehydration apparatus, 103.2 g of an ammonium salt of 1,4-cyclohexanedicarboxylic acid produced according to the method described in Example 1 (the content of ammonia in the ammonium salt of 1,4-cyclohexanedicarboxylic acid was 0.34 in a molar ratio based on the content of 1,4-cyclohexanedicarboxylic acid in the ammonium salt of 1,4-cyclohexanedicarboxylic acid), 0.40 g of zinc oxide (manufactured by Kanto Chemical Co., Inc.) as a catalyst, and 200 g of BARREL process oil B-28AN (manufactured by MATSUMURA OIL Co., Ltd.) were placed. Then, heating was started, and nitrogen gas (flow rate: 34 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 300 rpm for 8 hours to carry out a cyanation reaction. After the reaction finished, the reaction product was dissolved in tetrahydrofuran, and after further removing the catalyst in the solution by filtration, the reaction product was analyzed by gas chromatography (hereinafter, also described as GC) (model name "GC2010 PLUS" manufactured by Shimadzu Corporation, column: product name "HP-5ms" manufactured by Agilent Technologies, 30 m length×0.25 mm i.d., film thickness 0.25 μm). As a result, the yield of 1,4-dicyanocyclohexane was 92.1%.

Example 3

In a 300 mL five neck flask equipped with a stirring blade, a gas introduction tube, a thermocouple and a dehydration apparatus, 51.6 g of an ammonium salt of 1,4-cyclohexanedicarboxylic acid produced according to the method described in Example 1 (the content of ammonia in the ammonium salt of 1,4-cyclohexanedicarboxylic acid was 0.34 in a molar ratio based on the content of 1,4-cyclohexanedicarboxylic acid in the ammonium salt of 1,4-cyclohexanedicarboxylic acid), 0.20 g of zinc oxide (manufactured by Kanto Chemical Co., Inc.) as a catalyst, and 50 g of 1,4-dicyanocyclohexane were placed. Then, heating was started, and nitrogen gas (flow rate: 34 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 300 rpm for 7 hours to carry out a cyanation reaction. After the reaction finished, the same operation as in Example 2 was carried out, and analysis by GC was carried out. The yield of 1,4-dicyanocyclohexane was 90.8%.

Example 4

In a 100 mL five neck flask equipped with a stirring blade, a gas introduction tube, a thermocouple and a dehydration apparatus, 51.6 g of an ammonium salt of 1,4-cyclohexanedicarboxylic acid produced according to the method described in Example 1 (the content of ammonia in the ammonium salt of 1,4-cyclohexanedicarboxylic acid was 0.34 in a molar ratio based on the content of 1,4-cyclohexanedicarboxylic acid in the ammonium salt of 1,4-cyclohexanedicarboxylic acid) and 0.20 g of zinc oxide (manufactured by Kanto Chemical Co., Inc.) as a catalyst were placed. Then, heating was started, and nitrogen gas (flow rate: 34 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 300 rpm for 7 hours to carry out a cyanation reaction. After the reaction finished, the same operation as in Example 2 was carried out, and analysis by GC was carried out. The yield of 1,4-dicyanocyclohexane was 92.8%.

Example 5

The nucleus hydrogenation reaction was advanced in the same manner as Example 1, obtaining an aqueous ammonia solution including 30.11 g (0.174 mol; 8% by mass) of 1,4-cyclohexanedicarboxylic acid. Next, into a 100 mL four neck flask equipped with a stirring blade, a gas introduction tube, a thermocouple and a dehydration apparatus, the aqueous ammonia solution described above was added appropriately; the inside of the flask was heated at an ordinary pressure while stirring at 300 rpm; and the solution was concentrated at 110° C. over 3.5 hours until the concentration of 1,4-cyclohexanedicarboxylic acid reached 50% by mass. Then, 0.24 g of zinc oxide (Kanto Chemical Co., Inc.) as a catalyst was placed in the four neck flask, and the temperature was elevated from 110° C. to 170° C. over 49 minutes for concentration to obtain a heated concentrate. With the obtained heated concentrate left in the flask, the inside of the flask was continuously heated at an ordinary pressure while continuing the introduction of nitrogen gas at 20 mL/min and ammonia gas at 52 mL/min into the flask and stirring; the temperature was elevated to 280° C. over 15 minutes; and furthermore, the temperature was retained at that temperature for 6.4 hours to advance the cyanation reaction. After the reaction finished, the same operation as in Synthetic Example 2 was carried out, and analysis by GC was carried out. The yield of 1,4-dicyanocyclohexane was 89.1%.

Note that analytical conditions for GC were as follows.
Carrier gas: He (constant pressure: 73.9 kPa)
Inlet temperature: 300° C.
Detector: FID
Detector temperature: 300° C.
Column oven temperature: initially 100° C., elevated to 300° C. at 10° C./min, and retained at 300° C. for 30 mins)

Nitrile Hydrogenation Step

Example 6

In a 300 mL pressure resistant vessel made of SUS316, 24.4 g of 1,4-dicyanocyclohexane obtained by advancing the cyanation reaction in the same manner as Example 2, 37.3 g of methanol and 28.4 g of a 28% aqueous ammonia (manufactured by Wako Pure Chemical Industry Co., Ltd.) as solvents, and 0.56 g of Raney cobalt catalyst (manufactured by Wako Pure Chemical Industry Co., Ltd.) as a catalyst were placed, and hydrogen gas was introduced until reaching a reaction pressure of 4.5 MPa. Next, the inside of the vessel was heated to a reaction temperature of 80° C., and while retaining the constant temperature and stirring the inside of the vessel with an electromagnetic stirring blade at 750 rpm, the amination reaction through hydrogenation (nitrile hydrogenation reaction) was advanced for 240 minutes. As a result, the conversion rate of 1,4-dicyanocyclohexane was 100%, and the selectivity and the yield of 1,4-bis(aminomethyl)cyclohexane were 97.0% and 97.0%, respectively.

Example 7

In a 300 mL pressure resistant vessel made of SUS316, 38.2 g of 1,4-dicyanocyclohexane obtained by advancing the cyanation reaction in the same manner as Example 2, 111.6 g of liquid ammonia as a solvent, and 3.31 g of Raney cobalt catalyst (manufactured by Wako Pure Chemical Industry Co., Ltd.) as a catalyst were placed, and hydrogen gas was introduced until reaching a reaction pressure of 8.0 MPa. Next, the inside of the vessel was heated to a reaction temperature of 90° C., and while retaining the constant temperature and stirring the inside of the vessel with an electromagnetic stirring blade at 750 rpm, the amination reaction through hydrogenation (nitrile hydrogenation reaction) was advanced for 60 minutes. As a result, the conversion rate of 1,4-dicyanocyclohexane was 100%, and the selectivity and the yield of 1,4-bis(aminomethyl)cyclohexane were 99.4% and 99.4%, respectively.

After the reaction finished, the reaction solution was diluted with MeOH and then analyzed by GC (model name "GC-2010" manufactured by Shimadzu Science Co., column: product name "HP-5MS" manufactured by Agilent Technologies, 30 m length×0.25 mm i.d., film thickness 0.25 μm, conditions: carrier gas: He (constant pressure: 73.9 kPa), inlet temperature: 300° C., detector: FID, detector temperature: 330° C., column oven temperature: initially 120° C., retained for 10 mins, elevated to 300° C. at 10° C./min, and retained at 300° C. for 30 mins).

The present application is based on Japanese Patent Application No. 2018-076283 filed in the Japan Patent Office on Apr. 11, 2018, the contents of which are incorporated herein by reference.

Industrial Applicability

Since the cyclohexanedicarboxylic acid compound of the present invention can be a raw material for bis(aminomethyl)cyclohexane, which is effective as an optical material for a plastic lens, prism, optical fiber, information recording substrate, filter, etc., used for polyamide, polyurethane and the like, it has an industrial applicability in such fields.

The invention claimed is:

1. A method for producing a cyclohexanedicarboxylic acid compound, comprising:
    bringing a phthalic acid compound in an aqueous ammonia solution into contact with hydrogen in the presence of a fixed bed catalyst in a reactor such that a cyclohexanedicarboxylic acid compound or an aqueous ammonia solution of a cyclohexanedicarboxylic acid compound is obtained.

2. A method for producing a dicyanocyclohexane compound, comprising:
    obtaining a cyclohexanedicarboxylic acid compound via the method of claim 1; and
    subjecting the cyclohexanedicarboxylic acid compound or a heated concentrate of the aqueous ammonia solution of a cyclohexanedicarboxylic acid compound to a cyanation reaction.

3. The method according to claim 2, wherein at least a part of the aqueous ammonia solution of a cyclohexanedicarboxylic acid compound obtained in the obtaining of the cyclohexanedicarboxylic acid compound is used as an ammonia source for the obtaining of the dicyanocyclohexane compound.

4. The method according to claim 2, further comprising:
    heating the aqueous ammonia solution of a cyclohexanedicarboxylic acid compound to 100 to 200° C. to remove at least a part of the water in the aqueous ammonia solution such that the heated concentrate is obtained.

5. A method for producing a bis(aminomethyl)cyclohexane compound, comprising:
    obtaining a dicyanocyclohexane compound via the method of claim 2; and
    subjecting the dicyanocyclohexane compound to a hydrogenation reaction.

6. The method according to claim 3, further comprising:
    heating the aqueous ammonia solution of a cyclohexanedicarboxylic acid compound to 100 to 200° C. to remove at least a part of the water in the aqueous ammonia solution such that the heated concentrate is obtained.

7. A method for producing a bis(aminomethyl)cyclohexane compound, comprising:
    obtaining a dicyanocyclohexane compound via the method of claim 3; and
    subjecting the dicyanocyclohexane compound to a hydrogenation reaction.

8. A method for producing a bis(aminomethyl)cyclohexane compound, comprising:
    obtaining a dicyanocyclohexane compound via the method of claim 4; and
    subjecting the dicyanocyclohexane compound obtained to a hydrogenation reaction.

9. A method for producing a bis(aminomethyl)cyclohexane compound, comprising:
    obtaining a dicyanocyclohexane compound via the method of claim 6; and
    subjecting the dicyanocyclohexane compound to a hydrogenation reaction.

10. The method according to claim 2, further comprising:
    heating the aqueous ammonia solution of a cyclohexanedicarboxylic acid compound to 120 to 200° C. to remove at least a part of the water in the aqueous ammonia solution such that the heated concentrate is obtained,
    wherein the cyclohexanedicarboxylic acid compound is a 1,4-cyclohexanedicarboxylic acid compound.

11. The method according to claim 2, further comprising:
    heating the aqueous ammonia solution of a cyclohexanedicarboxylic acid compound to 140 to 200° C. to remove at least a part of the water in the aqueous ammonia solution such that the heated concentrate is obtained,
    wherein the cyclohexanedicarboxylic acid compound is a 1,4-cyclohexanedicarboxylic acid compound.

12. The method according to claim 1, wherein an amount of the phthalic acid compound is in a range of 2 to 20% by mass based on the aqueous ammonia solution.

13. The method according to claim 1, wherein an amount of ammonia in the aqueous ammonia solution is in a range of 200 to 400 mol % based on 100 mol % of the phthalic acid compound.

14. The method according to claim 1, wherein an amount of the phthalic acid compound is in a range of 2 to 20% by mass based on the aqueous ammonia solution, and an amount of ammonia in the aqueous ammonia solution is in a range of 200 to 400 mol % based on 100 mol % of the phthalic acid compound.

15. A method for producing a dicyanocyclohexane compound, comprising:
    obtaining a cyclohexanedicarboxylic acid compound via the method of claim 14; and
    subjecting the cyclohexanedicarboxylic acid compound or a heated concentrate of the aqueous ammonia solution of a cyclohexanedicarboxylic acid compound to a cyanation reaction.

16. The method according to claim 15, wherein at least a part of the aqueous ammonia solution of a cyclohexanedicarboxylic acid compound obtained in the obtaining of the cyclohexanedicarboxylic acid compound is used as an ammonia source for the obtaining of the dicyanocyclohexane compound.

17. The method according to claim 15, further comprising:
    heating the aqueous ammonia solution of a cyclohexanedicarboxylic acid compound to 100 to 200° C. to remove at least a part of the water in the aqueous ammonia solution such that the heated concentrate is obtained.

18. A method for producing a bis(aminomethyl)cyclohexane compound, comprising:
    obtaining a dicyanocyclohexane compound via the method of claim 15; and
    subjecting the dicyanocyclohexane compound to a hydrogenation reaction.

19. The method according to claim 15, further comprising:
    heating the aqueous ammonia solution of a cyclohexanedicarboxylic acid compound to 120 to 200° C. to remove at least a part of the water in the aqueous ammonia solution such that the heated concentrate is obtained,
    wherein the cyclohexanedicarboxylic acid compound is a 1,4-cyclohexanedicarboxylic acid compound.

20. The method according to claim 15, further comprising:
    heating the aqueous ammonia solution of a cyclohexanedicarboxylic acid compound to 140 to 200° C. to remove at least a part of the water in the aqueous ammonia solution such that the heated concentrate is obtained,
    wherein the cyclohexanedicarboxylic acid compound is a 1,4-cyclohexanedicarboxylic acid compound.

* * * * *